United States Patent [19]

Smith et al.

[11] 4,399,255

[45] Aug. 16, 1983

[54] ALLOY RAYON FIBERS OF REGENERATED CELLULOSE AND COPOLYMERIC ACRYLIC ACID SALTS

[75] Inventors: Frederick R. Smith, Toms Brook, Va.; Walter W. Toy, Lansdale; David Witiak, Yardley, both of Pa.

[73] Assignees: Avtex Fibers Inc., Valley Forge; Rohm & Haas Co., Philadelphia, both of Pa.

[21] Appl. No.: 416,760

[22] Filed: Sep. 10, 1982

Related U.S. Application Data

[63] Continuation-in-part of Ser. No. 219,134, Dec. 22, 1980, abandoned.

[51] Int. Cl.³ .................... C08L 1/02; A61F 13/20; D01D 5/22
[52] U.S. Cl. .................. 525/54.21; 523/334; 106/164; 106/165; 106/168; 106/171; 264/188; 264/190; 264/191; 264/194; 524/36
[58] Field of Search ................ 525/54.21; 523/333, 523/334; 526/238.21; 527/314, 315; 128/284, 285; 264/188, 190, 191, 194; 524/36

[56] References Cited

U.S. PATENT DOCUMENTS

| Re. 30,029 | 6/1979 | Smith | 525/54.23 |
|---|---|---|---|
| 2,337,398 | 12/1943 | Marsh et al. | 524/36 |
| 2,686,103 | 8/1954 | Charch | 524/36 |
| 2,784,052 | 3/1957 | Jacobson | 264/207 |
| 2,993,018 | 7/1961 | Steinlin | 264/184 |
| 4,165,743 | 8/1979 | Denning | 264/191 |
| 4,240,937 | 12/1980 | Allen | 524/35 |
| 4,263,244 | 4/1981 | Allen et al. | 264/168 |

*Primary Examiner*—John Kight, III
*Assistant Examiner*—Nathan M. Nutter
*Attorney, Agent, or Firm*—Arthur R. Eglington

[57] ABSTRACT

Alloy rayon fiber of regenerated cellulose and an at least partially neutralized copolymer of acrylic or methacrylic acid and a comonomer selected from an hydroxyalkyl ($C_2$–$C_6$) ester of such acid or a styrenic monomer. The copolymer is present in an amount effective to increase the fluid holding capacity of the fiber. Masses of the fibers are useful as surgical dressings, tampons and other fluid-absorbing articles.

22 Claims, No Drawings

ALLOY RAYON FIBERS OF REGENERATED CELLULOSE AND COPOLYMERIC ACRYLIC ACID SALTS

CROSS REFERENCE TO RELATED APPLICATIONS

This disclosure is a continuation in part of our pending application Ser. No. 219,134, now abandoned, filed Dec. 22, 1980.

BACKGROUND OF THE INVENTION

The present invention is directed to alloy fibers having high fluid-holding capacity, to shaped articles comprising such fibers, and to a method of preparing the fibers.

Known in the art are alloy fibers of regenerated cellulose and a contained substance capable of increasing the fluid-holding capacity of rayon fibers not containing an alloying component. "Alloy rayon fiber" thus refers to a fiber formed from a uniform mixture of an aqueous alkaline cellulose xanthate solution and a substance other than cellulose as contrasted with merely coating a fiber with the substance. "Fluid-holding capacity" is a measure of liquid taken up by a mass of such alloy fibers, including the liquid held within the interstices of a mass of the fibers and the liquid absorbed and adsorbed by the fibers.

In making high fluid-holding alloy rayon, wherein viscose suitable for spinning is prepared by well-known methods, it is also known to incorporate an acrylic polymer into the viscose, and then to spin the resulting mixture to form regenerated cellulosic fiber. Representative patents describing alloy rayon containing acrylic polymers for enhancing fluid-holding capacity are U.S. Pat. Nos. 3,844,287 (now Reissue No. 30,029), 4,066,584 and 4,104,214.

Examples of teachings of copolymer systems which have absorbency utility include the following U.S. patents:

A. U.S. Pat. No. 3,567,118—Shepherd et al, issued Mar. 2, 1971, teaching the topical treatment of both natural and synthetic fibers with a solution of certain hydrophilic copolymers to aid entrapment in the fiber matrix of additives such as fragrances. The hydrophilic copolymers include copolymers of unsaturated hydroxyalkyl acrylates and monocarboxylic acids such as acrylic and methacrylic acids.

B. U.S. Pat. No. 3,669,103—Harper et al, issued June 13, 1972 teaches formed articles of improved absorbency for aqueous body fluids comprising supports containing dry, solid, water-swellable, water-insoluble polymeric sorbents such as lightly cross-linked polyacrylates, poly-2-hydroxyethyl acrylates, polyvinylpyrrolidones, and acrylamide/acrylic acid copolymers. The particulate polymers are dispersed in a wood pulp slurry in a Fourdrinier paper-making machine.

C. U.S. Pat. No. 4,190,562—Westerman, issued Feb. 26, 1980, teaches a film-forming water absorbent interpolymer of copolymerizable carboxylic acids such as acrylic or methacrylic acid, acrylic esters and an acrylic nitrile or amide. Hydroxyethyl methacrylate acrylate and hydroxypropyl methacrylate are acceptable cross-linking comonomer esters.

High fluid-holding cellulosic fibers, based on the inclusion of the acrylic polymer systems commercially available, and not containing hydroxyalkyl groups, are characterized by undesirable losses to and interaction with, the aqueous acidic spin baths into which the fluid containing cellulosic and such acrylic polymers are regenerated to form alloy rayon fibers.

The spin bath usually is an aqueous solution of $H_2SO_4$, and $Na_2SO_4$, and sometimes contains other materials which may affect the spinning or fiber characteristics.

Such acrylic polymers lost from the cellulosic matrix during filament formation produce flocculates and/or agglomerates with spinning by-product materials. In turn, these become tacky, troublesome deposits in the spin bath system. The deposits are difficult to remove from the system and special procedures are required to deal with them.

OBJECTS AND SUMMARY

An object of this invention is to define novel high-fluid-holding cellulosic alloy fibers wherein the alloying component is a member of a new family of acrylic polymers, which alloy fibers maintain the absorbency of the acrylic based systems taught heretofore but avoid the tacky, troublesome deposits in the spin bath system to which known acrylic polymer modified viscose fibers spinning systems are susceptible.

A further object is to utilize more fully the potential of the subject acrylic polymers in building high fluid holding capacity into rayon fibers, and thus achieve improved economy of manufacturing Another object is to provide an article of manufacture containing alloy fibers of regenerated cellulose having high retention for body fluids.

The foregoing objects are accomplished in accordance with this invention by providing cellulosic fibers, such as viscose rayon, wherein an acrylic copolymer, novelly crafted to provide an essential and useful balance between viscose compatibility and substantial insolubility in spin bath, is homogeneously mixed and/or uniformly dispersed in desired amounts with viscose. The resulting mixture or solution is spinnable into rayon by well known methods so as to form a high-fluid-holding regenerated cellulosic alloy fiber.

The spin bath used in making the novel alloy fiber will be devoid of or contain minimal amounts of tacky contaminant as there are virtually no losses of acrylic polymer during regeneration of the viscose/acrylic polymer spun from the spinning jets, and during subsequent processing of the regenerated cellulosic fibers.

In summary, the acrylic copolymers comprise (a) at least one acid monomer selected from an acrylic acid or a methacrylic acid and (b) at least one comonomer selected from hydroxyalkyl ($C_2$–$C_6$) esters of said acids and styrenic monomers.

By "styrenic monomer" as used herein is meant styrene or any vinyl aromatic monomer having properties substantially equivalent to styrene when used as a comonomer in preparing the copolymers herein. "Styrenic monomers" thus include styrene and substituted styrenes such as the various alkyl- or halogen-substituted styrenes including the ortho, meta and para isomers thereof, for example: vinyl toluene, ethylstyrene, p-chlorostyrene, 2,4-dichlorostyrene, $\alpha$-methyl styrene and the like.

DETAILED DESCRIPTION

The monomer ratio (a:b) in the copolymer ranges from 95:5 to 50:50 by weight, preferably from 80:20 to 60:40. Choice of comonomer (b) for copolymerization with the acid monomer (a), the monomer ratio a:b and copolymer molecular weight will be guided by several considerations. These include: the viscosity and solubility of the copolymer in aqueous solution at different pH values and polymer concentrations, copolymer stability, degree of enhancement of fluid holding capacity, avoidance of formation of sticky deposits during alloy fiber formation, and the relative costs of the monomers and copolymer manufacture. Thus, for a given molecular weight, the solubility of the copolymer will increase as the pH is raised and will decrease as the proportion of comonomer (b) increases. Solubility will also decrease as the carbon content of comonomer (b) increases. For example, in a copolymer of a given acid monomer, molecular weight and monomer ratio, hydroxypropyl methacrylate and hydroxybutyl methacrylate will provide lower solubility than will the corresponding hydroxyethyl methacrylate, and styrene will introduce even lower solubility. Such lower solubilities are desirable under the acidic conditions of the spin bath for coagulating and regenerating cellulosic fibers, in order to avoid or minimize formation of sticky deposits of copolymer not incorporated into the fiber. However, the same copolymer must be sufficiently soluble under the alkaline conditions of the viscose for good admixture with the viscose. The rayon alloy fiber chemist fully understands and appreciates the foregoing considerations and can readily vary the aforementioned parameters to optimize the benefits of the invention, in light of the inventive aspects described herein and the skill of the art.

Among the specific acrylic polymers found useful in this invention are copolymers of acrylic or methacrylic acid with one or more of hydroxyethyl acrylate ("HEA"), hydroxyethyl methacrylate ("HEMA"), hydroxypropyl acrylate ("HPA") and styrene. When the esterifying alcohols are isomeric mixtures, the ester groups will be a mixture of the various isomers—e.g., hydroxypropyl acrylate will comprise a mixture of the 2-hydroxypropyl and 3-hydroxypropyl esters. These copolymers are usually prepared in an aqueous solution containing about 5 to 20 percent solids (polymer), and may be in acid form or in partially or completely neutralized form.

The copolymers may contain minor proportions—e.g., up to about 25 wt. percent—of other monomers, in addition to monomers (a) and (b), provided the type and amount are such as not to detract materially from the properties required for use in this invention. Appropriate other monomers include any monomers which are monofunctional to monomers (a) and (b) and therefore will not introduce cross-linking. Acceptable other monomers are esters of acrylic and methacrylic acids, such as the $C_1$-$C_{18}$ alkyl esters thereof, vinyl esters such as vinyl acetate, and vinyl halides such as vinyl chloride, and the like.

The copolymers are prepared in aqueous dispersion by conventional, free radical solution polymerization techniques to provide products having molecular weights (weight average) in the range of about 10,000 to about 500,000, preferably about 300,000 to about 400,000. Molecular weights substantially under 10,000 will not provide sufficient fluid-holding capacity, and molecular weights over 500,000 render the copolymer solutions too viscous for efficient and economical handling and incorporation into the viscose.

It has been observed that the copolymers as prepared are water soluble or marginally water soluble and over a relatively short period of time became irreversibly gelatinous. This unstable condition shortens the useful life of the copolymers and as a practical matter will make their use as alloying components of rayon uneconomic. This unstable condition can be prevented or controlled by at least partially neutralizing the copolymers simultaneously with or soon after formation in solution. Not only is the tendency to gellation eliminated or minimized thereby, but the marginally water soluble copolymers are solubilized and the viscosity of the solutions is maintained in a manageable range.

The copolymers should be preneutralized at least about 25 percent, i.e., at least about 25 percent of the carboxyl groups of the copolymer should be converted to water-solubilizing salt form, preferably by treatment of the copolymers with an alkali metal hydroxide (e.g., NaOH or KOH) or ammonium hydroxide. Generally, up to about 75 percent neutralization is sufficient; higher degrees of neutralization tend to unduly increase the viscosity of the solutions. Best results have been observed for about 50% to 75% neutralization with copolymers of the preferred molecular weight range, for solutions containing 5 to 20 wt. % of the neutralized copolymer. Thus, degree of neutralization will generally be in inverse proportion to molecular weight for solution of the same polymer solids, since both properties contribute to viscosity of the copolymer solutions.

The technique of controlled neutralization to provide stable polymers and polymer solutions is the subject of a copending application, filed simultaneously with this application in the name of David Witiak, entitled "Stabilized Polymer Compositions", Ser. No. 218,909. The latter application is incorporated herein by reference.

The present fibers may be produced by a process which includes the steps of adding an aqueous dispersion of the copolymer to viscose, spinning the mixture into fiber form in an acid spin bath, washing to remove adhering acid, desulfurizing and treating the fibers with a finish, and drying: the conditions being such that some of the carboxyl groups are converted to the sodium salt form, the fibers then having measurable fluid-holding capacity. These and other details of the fiber-forming process are well-known as described, for example, in U.S. Pat. No. 4,066,584 and 4,104,214.

Preferably, the alloy rayon fibers of the invention will contain about 5 to 40%, based on the weight of cellulose ("boc"), preferably 10 to 30%, of the copolymer, and the alloy fiber will be neutralized sufficiently to provide fluid-holding capacity of at least 5.5 cc/gram, as measured by the Syngyna test (described hereinafter). The fiber preferably is neutralized to the required extent by treatment with an alkali metal hydroxide, such as NaOH, or ammonium hydroxide, with the result that substantially all or a portion of the carboxyl groups of the copolymer are converted to the corresponding salts.

The fibers normally are treated to provide a lubricant finish of, for example, a water-soluble polyoxyethylene sorbitan mono-laurate, or similar nonionic polyoxyethylene sorbitan monester of higher fatty acid or other nonionic material. Other types of finishes known in the art may be used. The type and amount of fiber finish and the degree of conversion of carboxyl groups to carboxylate salt groups are selected such that the wet fibers have considerable resistance to compaction and tend to separate from each other after they have been squeezed together (to express excess water) under pressure and then released. Thus, when the fibers are dried they will show little tendency to adhere to neighboring fibers, and the product fibers after "opening" will be substantially nonbonded. Specifically, the proportion of finish and the proportion of the carboxyl groups which are in salt form (as the sodium salt) should be such that when a mass of the fibers is wetted with two or more times its dry weight and then dried, without tension, in air at 25° C., the resulting fibers are substantially non-adherent. A desirable fiber pH (measured on a 1% slurry of these lubricated fibers in deionized water) is in the range of about 5.5 to 9.0, preferably about 6 to 8.5. Generally, the fibers are of about 1.5 to 6 denier and the staple fiber length is in the range of about ⅜ to 5 inches, such as about 1½ inches.

The fiber may be crimped, as described, for instance, in Merion et al. U.S. Pat. No. 2,517,694; Textile Research Journal Vol. 23 pp. 137–157 and Man Made Fibers by Moncrief (6th Edition, 1975, publ. by John Wiley & Sons) pp. 191–193.

The fluid holding capacity is measured by the following procedure: The fibers are carded into web form and then separated into 2.5 gram portions each about 6 inches long. Each sub web portion is then individually rolled in the direction of its width to provide a roll six inches long (15.24 cm) and a string is looped about the center thereof. Each such roll is then folded on itself at the string loop and drawn into a ½ inch diameter (1.27 cm) tube within which it is compressed by a clamp and plunger, thus forming a tampon. The resulting tampons are removed, and allowed to stand for a period of about 30 minutes (during which the tampons recover to a bulk density of about 0.4 g/cc). They are then evaluated for their capacity to hold water by the Syngyna Method, essentially as described by G. W. Rapp in a June 1958 publication of the Department of Research, Loyola University, Chicago, Illinois, titled "A Comparison of the Absorptive Efficiency of the Commercial Catamenial Tampon." (See modified protocol below.) The allow fibers of the present invention are adapted for use in a variety of articles, such as surgical dressings, pads, and vaginal tampons, in which high fluid holding retention is an essential characteristic. In the manufacture of such articles, the alloy fibers may be used in the same manner and with the same equipment as employed with other commercial fibers, including regular rayon. They may be blended with other fibers which may or may not enhance the absorbent properties of the resulting articles.

Staple fibers with which the alloy fibers of the present invention may be blended include, for example, rayon, cotton, chemically modified rayon or cotton, cellulose acetate, nylon, polyester, acrylic, polyolefin, etc. Typically, a tampon is an elongated cylindrical mass of compressed fibers, which may be supplied within a tube which serves as an applicator; see U.S. Pat. Nos. 2,024,218; 2,587,717; 3,005,456; 3,051,177.

The following examples are intended as further illustrations of the invention, but not as limitations on the scope thereof, except as set forth in the appended claims. All parts and percentages are by weight unless otherwise specified.

EXAMPLES AND TABLES

EXAMPLE I

Preparation of Acrylic acid/hydroxyethyl methacrylate (80/20 wt. %) Copolymer. Into a 5-liter 3-neck round bottom flask is charged 2960 ml of deionized (DI) water. The water is heated with a heating mantle to 85°–87° C. while being stirred with a mechanical stirrer. While this is being done, 416 g. of acrylic acid (AA) and 104 g. of 2-hydroxyethyl methacrylate (HEMA) are charged into a one-liter graduated separatory funnel. A 1 wt. % aqueous solution of ammonium persulfate (APS) is also prepared. When the temperature of the water levels off at 85°–87° C., 13 ml of the 1 wt. % APS solution is added to the reactor. The monomer solution and a co-feed catalyst of 52 ml of the 1 wt. % APS solution are then added gradually and proportionally to the reactor over a period of about two hours. During the addition the temperature is maintained at 85°–87° C. and agitation is increased gradually to maintain good stirring.

After the additions are completed the polymer solution is held at 85°–87° C. for 30 minutes. At the end of the 30-minute time period, an additional catalyst system consisting of 0.4 g. of tertiary butyl hydroperoxide diluted in 10 ml of DI water and 0.3 g of sodium sulfoxylate formaldehyde dissolved in 10 ml of DI water are added. Stirring is continued for 30 minutes. A neutralizer consisting of 232 g of 50% sodium hydroxide is added. Stirring is continued for about 30 minutes. The product obtained is a clear solution with a viscosity of about 7000 cps. at 20° C.±2° C. (Brookfield Viscometer, 12 rpm spindle 3) and has a polymer solids content of 15.4% with about 50% of the acid groups neutralized.

EXAMPLE II

The copolymer solution in water, prepared as described in Example I, a viscous liquid, containing about 15% of the copolymer of acrylic acid and hydroxyethyl methacrylate (HEMA), was injected into viscose so that the resulting solutions of viscose and copolymer at the spinning jet contained 15, 20 and 25 percent of copolymer (calculated as fully neutral salt), based on cellulose (boc) in the viscose. During blending, the mixture is subjected to mechanical shearing. The composition of the viscose (prior to blending) is 9.6 percent cellulose, 6.2 percent sodium hydroxide and 31 percent (based upon the weight of the cellulose) carbon disulfide. The viscose ballfall viscosity is 60 and its common salt test is 7.

The spin bath contained 7.6 percent $H_2SO_4$, 21 percent $Na_2SO_4$ and one percent $ZnSO_4$ at 55°. The stretch bath contained 5 percent $H_2SO_4$ and 10 percent $Na_2SO_4$ and the stretch was 70 percent. The fiber was collected, cut to about 1½ inch lengths, washed successively in hot water—20 minutes, 0.5 percent NaOH—10 minutes, water—5 minutes for each of four washings, and finally washed in a solution containing 0.3 percent AHCO (R) 7596T solution. (AHCO is a trademark of ICI America for a series of polyoxyethylene adducts of sorbitan monesters of higher fatty acids. AHCO 7596T is the lauric acid derivative.) A portion of the fiber produced from the solution containing 20 percent polymer (boc) was set aside in an acid form, that is, after the fibers were washed but before neutralization. This portion is identified as sample D. The fiber samples were dried, conditioned at 70° C. and 65 percent relative humidity and tested, giving results as follows (Table I) wherein samples II-A, II-B, and II-C are the fibers prepared from the viscose solutions containing 15, 20 and 25 percent, respectively, of the acrylic copolymer salt.

EXAMPLE III

The fiber sample portion D set aside in acid state, as described in Example II, was treated twice in 0.5 percent $H_2SO_4$ to assure substantially complete conversion of the contained polymer to the acid form. The sample was then washed with water to remove the $H_2SO_4$. Portions of the sample (except a control sample portion 1) were individually treated with dilute NaOH solution, varying the concentration to achieve different degrees of neutralization. The resulting fibers were washed, and a finish was applied as in Example II. The fibers were then dried. The control sample portion 1 (acid state) was similarly dried. Each sample portion was evaluated in the Syngyna test with results as shown in Table II.

This experiment shows the importance of substantial conversion of the fiber to the neutralized form, in this case the sodium salt, in that at least partial neutralization is required to increase the fluid holding capacity over that exhibited by alloy fiber containing essentially unneutralized acrylic polymer.

EXAMPLE IV

Copolymers of AA/HEMA were prepared as in Example I by varying the monomer ratio to increase HEMA content. The absorbency values for the fibers made from viscose with these copolymers are presented in Table III. (Fiber samples II-B, III-B, III-C, and III-D).

Alternately, when HPMA, HEA and HPA were substituted for HEMA as the minor monomer of the copolymer and polymerized with AA, the below-listed copolymers were obtained. (Fiber samples III-E through III-H).

Likewise, when methacrylic acid was substituted for acrylic acid in the synthesis procedure of Example I, the corresponding listed products were prepared. (Fiber samples III-I and III-J). Similarly, a copolymer of acrylic acid was prepared with styrene as the comonomer, spun into a fiber and evaluated for fluid holding capacity. (Fiber Sample III-K).

Table III presents Syngyna test results for the foregoing alloy fibers of the invention (fiber samples III-B to III-K) as compared with alloy fiber sample II-B of Table II and a regular, non-alloyed fiber sample III-L as control. The alloy fibers were prepared substantially as described in Example II from a fluid containing viscose and containing 20 percent polymer (boc). It can be seen that the copolymer substantially increased the fluid holding capacity of the fibers.

EXAMPLE V

The effect of the acidic spin bath on some of the polymers used in forming the alloy fibers of the invention was studied, as compared to polyacrylic acid as a control. In each case, the polymers were in 50 percent neutralized form (sodium salts). A small pocket was fashioned by folding filter paper. One or two grams of a polymer solution was placed in the pocket and the pocket was then suspended in a synthetic spin bath, containing 7 percent $H_2SO_4$ and 21 percent $Na_2SO_4$. After 30 minutes the pocket was removed and contents examined and classified according to appearance (stringy, gel or curd) and touch (stickiness). See Table IV.

SYNGYNA TEST PROTOCOL

The Syngyna apparatus has been modified from that described by Rapp in that the liquid supply means is now a syringe pump which supplies liquid to the tampon at a fixed rate of 0.92 milliliters per minute. When the end of the test is observed, the volume of liquid delivered is divided by the known weight of the tampon and the quotient is recorded.

TABLE I

| AA/HEMA | Polymer Percent (boc) | Syngyna Value cc/g | Water Retention Percent | Saline Retention Percent | Saline pH |
|---|---|---|---|---|---|
| Sample II-A | 15 | 5.45 | 154 | 135 | 6.7 |
| Sample II-B | 20 | 6.05 | 180 | 152 | 6.8 |
| Sample II-C | 25 | 5.67 | 195 | 159 | 6.6 |
| Control | Regular Rayon | 3.8–4.2 | 110 | — | — |

TABLE II

| | AA/HEMA: 80/20 | | | | | |
|---|---|---|---|---|---|---|
| Fiber Sample Portion D | 1 | 2 | 3 | 4 | 5 | 6 |
| Syngyna cc/g | 3.89 | 5.16 | 5.82 | 6.04 | 6.05 | 6.35 |
| Saline pH | 3.04 | 4.35 | 4.96 | 5.32 | 5.87 | 6.61 |
| Degree of neutralization | .05 | .36 | .56 | .66 | .79 | .92 |

TABLE III

| Fiber Sample | Major Monomers | Minor Monomers | Copolymer (Monomer Ratios) | Syngyna Values (Average Three) |
|---|---|---|---|---|
| II-B | Acrylic Acid (AA) | Hydroxyethyl Methacrylate (HEMA) | AA/HEMA 80/20 | 6.0 |
| III-B | Acrylic Acid (AA) | Hydroxyethyl Methacrylate (HEMA) | AA/HEMA 70/30 | 6.0 |
| III-C | Acrylic Acid (AA) | Hydroxyethyl Methacrylate (HEMA) | AA/HEMA 65/35 | 6.4 |
| III-D | Acrylic Acid (AA) | Hydroxyethyl Methacrylate (HEMA) | AA/HEMA 60/40 | 6.6 |
| III-E | Acrylic Acid (AA) | Hydroxyethyl Methacrylate (HPMA) | AA/HPMA 80/20 | 6.42 |
| III-F | Acrylic Acid (AA) | Hydroxypropyl Methacrylate (HPMA) | AA/HPMA 90/10 | 6.33 |
| III-G | Acrylic Acid (AA) | Hydroxyethyl Acrylate (HEA) | AA/HEA 80/20 | 6.57 |
| III-H | Acrylic Acid (AA) | Hydroxypropyl Acrylate (HPA) | AA/HPA 80/20 | 5.64 |
| III-I | Methacrylic Acid (MAA) | Hydroxyethyl Methacrylate (HEMA) | MAA/HEMA 80/20 | 5.75 |
| III-J | Methacrylic Acid (MAA) | Hydroxypropyl Methacrylate (HPMA) | MAA/HPMA 80/20 | 5.25 |
| III-K | Acrylic Acid (AA) | Styrene (STY) | AA/STY 85/15 | 6.2 |
| III-L | None | None | None | 3.8–4.2 |

TABLE IV

PROPERTIES OF RESIDUE FROM POLYMER/SPIN BATH INTERACTION

| POLYMER | RATIO | APPEARANCE OF RESIDUE | TACTILE |
|---|---|---|---|
| AA/HEMA | 80/20 | gel, stringy | non sticky |
| AA/HEMA | 70/30 | gel, curd | non sticky |
| AA/HEMA | 65/35 | gel, curd | non sticky |
| AA/HEMA | 60/40 | gel, curd | non sticky |
| AA/HPMA | 80/20 | stringy | non sticky |
| AA/HPMA | 90/10 | stringy | sticky |
| AA/HEA | 80/20 | elastic gel | non sticky |
| AA/HPA | 80/20 | curd | non sticky |
| MAA/HEMA | 80/20 | gel | non sticky |

TABLE IV-continued

PROPERTIES OF RESIDUE FROM POLYMER/SPIN BATH INTERACTION

| POLYMER | RATIO | APPEARANCE OF RESIDUE | TACTILE |
| --- | --- | --- | --- |
| MAA/HPMA | 80/20 | gel | non sticky |
| AA/MAA | 50/50 | stringy | sticky |
| AA | — | stringy | extremely sticky |

We claim:

1. Alloy rayon fiber comprising regenerated cellulose and an at least partially neutralized copolymer of (a) at least one acid monomer selected from acrylic acid and methacrylic acid, and (b) at least one comonomer selected from hydroxyalkyl $C_2$–$C_6$) esters of said acids and a styrenic comonomer, the monomer ratio (a:b) in the copolymer ranging from 95:5 to 50:50 by weight, said copolymer being present in an amount effective to provide a measurable fluid holding capacity increase for the alloy fiber.

2. The alloy fiber of claim 1 wherein the monomer ratio (a:b) ranges from 80:20 to 60:40.

3. The alloy fiber of claim 1 wherein the fiber is at least partially neutralized with an alkali metal hydroxide.

4. The alloy fiber of claim 3 wherein the fiber is neutralized to an extent effective to provide of at least 5.5 cc./g. in the Syngyna test, said copolymer being present in an amount effective to provide a measurable fluid holding capacity increase for the alloy fiber.

5. The alloy fiber of claim 2 wherein the fiber contains about 5 to 40%, based on the weight of regenerated cellulose, of said copolymer, said copolymer being neutralized to at least 45 percent.

6. The alloy fiber of claim 5 wherein the nautralized copolymer is in alkali metal or ammonium salt form.

7. The alloy fiber of claim 5 wherein comonomer (b) is at least one of the hydroxyethyl and hydroxypropyl esters of at least one of acrylic and methacrylic acids.

8. The alloy fiber of claim 5 wherein the copolymer is an acrylic acid/hydroxyethyl methacrylate copolymer.

9. The alloy fiber of claim 5 wherein the copolymer is an acrylic acid/hydroxypropyl methacrylate copolymer.

10. The alloy fiber of claim 5 wherein the copolymer is an acrylic acid/hydroxyethyl acrylate copolymer.

11. The alloy fiber of claim 5 wherein the copolymer is an acrylic acid/hydroxypropyl acrylate copolymer.

12. The alloy fiber of claim 5 wherein the copolymer is a methacrylic acid/hydroxyethyl methacrylate copolymer.

13. The alloy fiber of claim 5 wherein the copolymer is a methacrylic acid/hydroxypropylmethacrylate copolymer.

14. The alloy fiber of claim 5 wherein the copolymer is an acrylic acid/styrenic copolymer.

15. The alloy fiber of claim 5 wherein the copolymer is an acrylic acid/styrene copolymer.

16. A method of producing an alloy fiber having high fluid holding capacity while avoiding or minimizing loss of polymer additive, which comprises: (1) mixing with a filament forming viscose a copolymer of (a) at least one acid monomer selected from acrylic acid and methacrylic acid, and (b) at least one comoner selected from hydroxyalkyl ($C_2$–$C_6$) esters of said acids and a styrenic comonomer, the monomer ratio (a:b) in the copolymer ranging from 95:5 to 50:50 by weight; (2) forming the mixture into a fiber; (3) coagulating and regenerating the fiber in an acid bath; and (4) at least partially neutralizing the regenerated fiber, said copolymer being present in an amount effective to provide a measurable fluid holding capacity increase for the alloy fiber.

17. The method of claim 16 wherein the regenerated fiber is subjected to application of a lubricating and protective finish for cellulose.

18. The method of claim 17 wherein the finished fiber is subjected to drying in an alkaline state.

19. Alloy rayon fiber produced by the method of claim 16.

20. An article of manufacture comprising a mass of alloy fibers as defined in claim 5.

21. The article of claim 19 wherein the mass of alloy fibers comprises a non-woven array.

22. The article of claim 19 in the form of a surgical dressing.

* * * * *

UNITED STATES PATENT AND TRADEMARK OFFICE
CERTIFICATE OF CORRECTION

PATENT NO. : 4,399,255
DATED : August 16, 1983
INVENTOR(S) : Frederick R. Smith et al.

It is certified that error appears in the above-identified patent and that said Letters Patent is hereby corrected as shown below:

Column 1, line 61, delete "acrylate"

Column 5, line 37, correct spelling of "allow" to -- alloy --

Column 10, line 23, correct spelling of "comoner" to -- comonomer --

Signed and Sealed this

Twenty-seventh Day of December 1983

[SEAL]

Attest:

GERALD J. MOSSINGHOFF

Attesting Officer    Commissioner of Patents and Trademarks